(12) United States Patent
Graber

(10) Patent No.: US 12,728,225 B2
(45) Date of Patent: Sep. 8, 2026

(54) COMBINATION ENDOTRACHEAL TUBE STYLET WITH MEDICATION ATOMIZATION SYSTEM

(71) Applicant: THE REGENTS OF THE UNIVERSITY OF CALIFORNIA, Oakland, CA (US)

(72) Inventor: Taylor J. Graber, Scottsdale, AZ (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 940 days.

(21) Appl. No.: 17/797,097

(22) PCT Filed: Mar. 9, 2021

(86) PCT No.: PCT/US2021/021556
§ 371 (c)(1),
(2) Date: Aug. 2, 2022

(87) PCT Pub. No.: WO2021/183550
PCT Pub. Date: Sep. 6, 2021

(65) Prior Publication Data

US 2023/0058976 A1 Feb. 23, 2023

Related U.S. Application Data

(60) Provisional application No. 62/987,071, filed on Mar. 9, 2020.

(51) Int. Cl.

| | |
|---|---|
| ***A61M 19/00*** | (2006.01) |
| ***A61M 11/00*** | (2006.01) |
| ***A61M 16/04*** | (2006.01) |

(52) U.S. Cl.
CPC .......... *A61M 19/00* (2013.01); *A61M 11/007* (2014.02); *A61M 16/0488* (2013.01); *A61M 2202/048* (2013.01)

(58) Field of Classification Search
CPC ........................ A61M 16/0488; A61M 11/007
See application file for complete search history.

(56) References Cited

U.S. PATENT DOCUMENTS 2,541,402 A * 2/1951 Caine .................. A61B 1/2676 128/200.26
4,182,326 A 1/1980 Ogle
(Continued)

FOREIGN PATENT DOCUMENTS

AU 2016213800 A1 9/2016

OTHER PUBLICATIONS

Haas, C., et al., Endotracheal Tubes: Old and New, Respiratory Care, Jun. 2014, pp. 933-955, vol. 59.
(Continued)

*Primary Examiner* — Bradley H Philips
(74) *Attorney, Agent, or Firm* — Eleanor Musick; Torrey Pines Law Group PC

(57) ABSTRACT

A combination stylet device for use in guiding an endotracheal tube during an intubation procedure includes an elongated hollow sleeve having a fitting at one end configured for mating with a syringe and a nozzle at the second end for generating a fine spray of a liquid forward from the second end. An elongated bendable guiding stylet is disposed coaxially within the sleeve to define a channel through which pressurized liquid is conducted from the fitting to the nozzle. The sleeve is inserted into the endotracheal tube during intubation to guide the insertion and to allow for administration a medication from the end of the endotracheal tube.

14 Claims, 8 Drawing Sheets

(56) References Cited

U.S. PATENT DOCUMENTS

| | | | | |
|---|---|---|---|---|
| 4,402,684 | A * | 9/1983 | Jessup ............... | A61M 25/0102 128/207.14 |
| 5,257,620 | A * | 11/1993 | Schermerhorn .. | A61M 16/0463 128/200.26 |
| 5,730,123 | A * | 3/1998 | Lorenzen .............. | A61M 39/26 128/207.14 |
| 6,112,743 | A * | 9/2000 | Denton .................. | A61M 11/06 128/200.14 |
| 6,698,429 | B2 * | 3/2004 | Croll ................. | A61M 16/0486 128/207.14 |
| 7,389,947 | B2 | 6/2008 | Denton | |
| 10,335,559 | B2 | 7/2019 | Herskovic | |
| 10,888,260 | B2 | 1/2021 | Edelhauser et al. | |
| 2002/0108614 | A1 | 8/2002 | Schultz | |
| 2005/0235998 | A1 | 10/2005 | Tresnak et al. | |
| 2006/0081253 | A1 | 4/2006 | Nelson | |
| 2012/0184921 | A1 * | 7/2012 | Brillant ............. | A61M 16/0484 604/533 |
| 2013/0167839 | A1 * | 7/2013 | Vomastek ......... | A61M 16/0488 128/200.26 |
| 2017/0182265 | A1 * | 6/2017 | Herskovic ......... | A61M 5/16881 |

OTHER PUBLICATIONS

PCT/US2021/021556 International Search Report and Written Opinion, Jun. 22, 2021, 8 pages.

* cited by examiner

COMBINATION ENDOTRACHEAL TUBE STYLET WITH MEDICATION ATOMIZATION SYSTEM

RELATED APPLICATIONS

This application is a 371 national stage filing of International Application No. PCT/US2021/021556, filed Mar. 9, 2021, which claims the benefit of the priority of U.S. Application No. 62/987,071, filed Mar. 9, 2020, each of which is incorporated herein by reference in its entirety.

FIELD OF THE INVENTION

The present invention relates to an endotracheal tube having a combined guiding stylet and medication atomization system for use in an intubation procedure.

BACKGROUND OF THE INVENTION

Endotracheal intubation is one of the more common procedures performed in hospitals and in emergency situations generally, yet it can still present challenges to even the most experienced practitioners. Difficult intubation, defined by more than two intubation attempts, is associated with life-threatening complications. These challenges have led to the development of enhanced devices, e.g., add-ons to the endotracheal tube (ETT), and procedures, including identifying risk factors for difficult intubation. One significant device improvement is the stylet, which is a rigid but malleable introducer that fits inside the ETT and allows for manipulation of the tube shape, usually into a hockey stick shape, to facilitate passage of the tube through the laryngeal inlet. The stylet also provides additional rigidity to the tube which may aid in tube passage.

Another function that has been added to ETTs is the ability to administer medications to the patient while intubated. Medications such as epinephrine, atropine, diazepam, and naloxone have shown rapid and efficacious pharmacodynamics when administered via ETT. This capability is particularly beneficial in cardiac arrest situations when there is not an existing intravenous cannula to supply intravenous medications.

The prior art includes well-documented examples of endotracheal tubes with inner inserted stylets, such as that shown in FIGS. 1-3, the purpose of which is to guide the tube during intubation or placement within trachea (windpipe) of the patient in order to maintain an open airway or to serve as a conduit through which to administer certain drugs. An example of a typical endotracheal tube (ETT) 6 is depicted in FIG. 1 and includes an upper proximal end 5 and an inserting and distal end 11. Upon being located at the correct position during such as the intubation process, an inflatable cuff 7 located near the distal end is expanded through a separate line terminating at proximal end nipple 9. Once inflated, cuff 7 keeps the ETT 6 at the desired location in the trachea while maintaining a sealed airway to deliver positive pressure ventilation and prevent aspiration of gastric or oropharyngeal contents.

FIG. 2 provides an example of a prior art laryngotracheal cannula device that provides for the administration of medication. As shown, a plastic or glass cylinder or vial 12 disposed near the proximal end of cannula 14 may contain a volume of an anesthetic composition such as Lidocaine. Cannula 14 has a plurality of apertures 10 formed near its distal end 11 to release the medication. This cannula is designed to be used prior to placement of the ETT but is not designed to be used in conjunction with the ETT during placement. Furthermore, the design of existing laryngotracheal cannulation devices do not provide for the injection of medications that are not pre-filled into the vial. As a result, there is no mechanism by which a clinician can introduce other medications to inject into the trachea other than lidocaine, such as which may be beneficial in cardiac arrest situations when there is not an existing intravenous cannula to supply intravenous medications.

FIG. 3 illustrates a prior art guiding stylet 15, which typically consists of a malleable metal wire designed to be inserted into the center of endotracheal tube 6 to add rigidity to the tube so that it conforms better to the upper airway anatomy of the specific individual and assist in successful placement. The proximal end of the guiding stylet 15 is usually bent on insertion into the ETT to form an abutment shoulder which acts as an abutment stop relative to the inserting upper end 5 of the ETT 6, thereby preventing over-insertion of the stylet which could result in the stylet projecting beyond the distal end 11 of the ETT, presenting the risk of perforation of the trachea.

The existing laryngotracheal cannulation device of FIG. 2 is not long enough to span the full length of the endotracheal tube 6 and, therefore, cannot be placed inside of the endotracheal tube 6 alongside an existing guiding stylet. As a result, practitioners must locate the tracheal aperture and vocal cords and then perform two separate motions, first positioning the laryngotracheal cannulation device to anesthetize the vocal cords and trachea, then placing the endotracheal tube with the guiding stylet. The use of two separate devices increases clinical time and can potentially lead to patient decompensation during an intubation. Accordingly, the need remains for a single device capable of performing multiple functions for intubation.

SUMMARY OF THE INVENTION

The inventive device provides the attributes of a stylet and a mucosal atomization system into a combination assembly configured for insertion into an endotracheal tube to facilitate an intubation procedure. When placed within an ETT during insertion into the patient's trachea, the assembly performs the dual functions of guiding the endotracheal tube and facilitating the administration of a medication to assist in more efficiently anesthetizing the insertion region (vocal cords, larynx, and trachea before and during the intubation procedure.

In one aspect of the invention, a combination stylet device for use in guiding an endotracheal tube during an intubation procedure includes an elongated hollow sleeve having a fitting at one end configured for mating with a syringe and a nozzle at the second end for generating a fine spray of a liquid. An elongated bendable guiding stylet is disposed coaxially within the sleeve to define a channel through which pressurized liquid is conducted from the fitting to the nozzle. The sleeve is inserted into the endotracheal tube during intubation to guide the insertion and to allow for administration a medication from the end of the endotracheal tube.

In an exemplary embodiment, a syringe is connected at the proximal end to a Luer-style fitting that is configured for releasable attachment to a syringe or medication reservoir, which may contain a liquid such as a topical anesthesia. The fitting is connected to the proximal end of an elongated sleeve that coaxially encases a flexible guiding stylet which imparts flexibility and rigidity to the assembly. A channel defined between the inner wall of the sleeve and the guiding stylet communicates liquid from the proximal end to the distal end of the assembly. The sleeve terminates at a nozzle tip that is configured to release an atomized spray of liquid that was communicated, under pressure, through the channel. The assembly is configured for insertion into an endotracheal tube to guide intubation and to provide for administration of a liquid spray from the end of the assembly.

In another aspect of the invention, the combination stylet device for use in guiding an endotracheal tube during an intubation procedure includes an elongated sleeve having a hollow interior; a fitting disposed at a proximal end of the sleeve, the fitting having a connector opening configured for mating with a syringe; a nozzle disposed at a distal end of the sleeve, the nozzle configured to generating a fine spray of a liquid forward of the distal end; and an elongated bendable guiding stylet disposed coaxially within the sleeve between the fitting and the nozzle, wherein a channel is defined between an outer surface of the guiding stylet and an inner surface of the sleeve, and wherein liquid introduced under pressure through the fitting is communicated by the channel to the nozzle; wherein the sleeve is configured for insertion into the endotracheal tube during intubation, the sleeve having a length configured to position the nozzle near a distal end of the endotracheal tube. In some embodiments, the fitting is configured for releasable attachment to the syringe, and wherein the syringe generates sufficient pressure to force liquid in the syringe out of the nozzle. The liquid may be a topical anesthetic.

In some embodiments, the fitting may further include an insertion stop configured to limit a length of insertion length within the endotracheal tube. The fitting may be a Luer-style fitting configured for releasably mating with a Luer-style syringe. A connector may be disposed at an end of an elongated tubing, configured for releasably mating with the fitting where the elongated tubing has a length configured to allow administration of additional liquids at a non-interfering distance from the intubation procedure. In some embodiments, a removable stop may be provided for attachment to the fitting or the sleeve to limit insertion of the device to a predetermined insertion depth within the endotracheal tube.

In still another aspect of the invention, a stylet device for guiding an endotracheal tube during intubation includes an elongated cylindrical sleeve having a hollow interior, the sleeve formed from a flexible medical grade plastic material; an elongated bendable guiding stylet disposed coaxially within the sleeve, the guiding stylet having an outer diameter smaller than an inner diameter of the sleeve so that a channel is defined between the guiding stylet and the sleeve; a fitting disposed at a proximal end of the sleeve to define a liquid-tight seal, the fitting having a connector opening configured for mating with a syringe; and a nozzle disposed at a distal end of the sleeve, the nozzle configured to generating a fine spray of a liquid forward of the distal end when a pressure is applied at the proximal end of the sleeve; wherein the sleeve is configured for coaxial insertion into the endotracheal tube during intubation, the sleeve having a length configured to position the nozzle near a distal end of the endotracheal tube. In some embodiments, the fitting is configured for releasable attachment to the syringe, and wherein the syringe generates sufficient pressure to force liquid in the syringe out of the nozzle. The liquid may be a topical anesthetic.

In some embodiments, the fitting may further include an insertion stop configured to limit a length of insertion length within the endotracheal tube. The fitting may be a Luer-style fitting configured for releasably mating with a Luer-style syringe. A connector may be disposed at an end of an elongated tubing, configured for releasably mating with the fitting where the elongated tubing has a length configured to allow administration of additional liquids at a non-interfering distance from the intubation procedure. In some embodiments, a removable stop may be provided for attachment to the fitting or the sleeve to limit insertion of the device to a predetermined insertion depth within the endotracheal tube.

DETAILED DESCRIPTION OF EMBODIMENTS

The inventive assembly combines the attributes of prior art stylets and laryngo-tracheal anesthetizing cannula for insertion within an endotracheal tube (ETT) during intubation. The combination assembly can be used to manipulate and guide the ETT from its interior during insertion within the patient's trachea, in combination with more efficiently anesthetizing the insertion region (vocal cords, larynx, and trachea) both before, during, and potentially after the intubation procedure.

Figures 1, 2, 3:
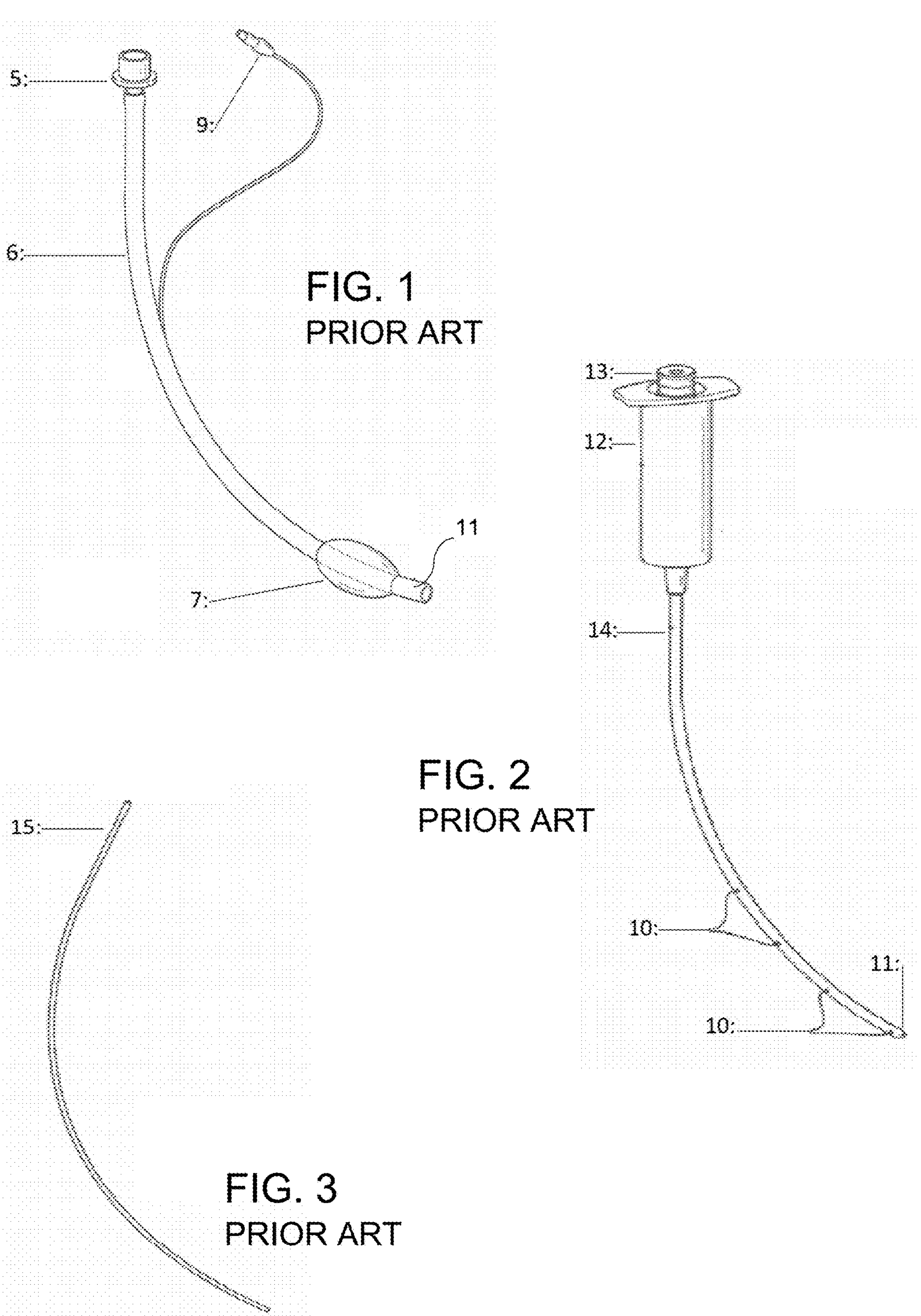
FIG. 1 is a perspective view of an exemplary endotracheal tube according to the prior art.
FIG. 2 is a perspective view of an exemplary prior art laryngotracheal cannula with a medicinal vessel.
FIG. 3 is a perspective view of an exemplary endotracheal-tube form guiding stylet according to the prior art.

For purposes of the description herein, the inventive assembly, illustrated in FIGS. 4-11, is alternately referred to as "the device", "the ETT stylet", or simply "the stylet", which is to be distinguished from conventional prior art stylets, such as the example shown in FIG. 3.

The inventive ETT stylet 40 is a generally cylindrical elongated body into which is integrated a medication delivery. Referring to FIGS. 4A, 4B, 5, 6A and 6B, stylet 40 includes a Luer-style fitting 42 with an opening 41 configured to mate with a standard syringe or other medication reservoir (not shown) for introducing liquid medication into the device. A medicinal syringe can be drawn according to the clinician's preferences and rapidly attached to fitting 42, which, in the exemplary embodiment, is a Luer-style fitting, e.g., a Luer-Lock® connector (Becton Dickinson). This medicinal syringe can be filled with any number of medications, such as but not limited to a fluidic topical anesthetic such as Lidocaine. The present invention also contemplates the use of other pharmacological agents to deliver medication via the trans-tracheal route under certain conditions, and such as where an intravenous route is either unavailable or inappropriate.

It should be noted that while a Luer-style fitting is described with reference to the exemplary embodiments, those of skill in the art will recognize that other fluid attachment devices, including conventional commercial and specially designed connectors, may be used.

In the exemplary embodiment, fitting 42 includes a flange 55 extending radially from the central body and a cylindrical extension 43 at its distal end that inserts into the proximal end of sleeve 44. Sleeve 44 is a hollow tube formed from flexible, resilient medical-grade plastic such as silicone, polydimethylsiloxane (PDMS), or similar bio-compatible material that is generally appropriate for medical applications. Typical properties of sleeve 44 include a smooth, low friction exterior surface with sufficient rigidity to resist crimping but sufficient flexibility and resilience to conform to the shape defined by the guiding stylet. Sleeve 44 is dimensioned to coaxially receive an elongated malleable guiding stylet 46 which extends most of the length of the sleeve. In some embodiments, guiding stylet 46 is loosely retained within sleeve 44, i.e., unattached to the inner surface of sleeve and cylindrical extension 43. Referring to FIG. 4B, the inner diameter of sleeve 44 and the outer surface of guiding stylet 46 define a channel 45 that extends the length of the sleeve, allowing liquid introduced via opening 41 in fitting 44 to be passed through channel 45 and out through atomization nozzle 50. In other embodiments, guiding stylet may be attached to extension 43 or partially attached at points within the interior surface of sleeve 44 as long as a channel is still present to allow fluid to by communicated the along the length of the sleeve. Nozzle 50 fits tightly within the distal end 48 of sleeve 44, i.e., a liquid-tight seal, so that liquid within channel 45 is forced through small bore 52 to generate a fine mist or spray 56 (shown in FIG. 5) that exits the distal end of the device. Pressure to force the liquid through bore 52 is provided by the syringe that is used to inject the liquid into fitting 42.

A process for manufacturing the inventive device may involve molding or extrusion of the sleeve body followed by assembly to affix the nozzle, guiding stylet, and fitting into the sleeve. Note that the nozzle and fitting may be stabilized within the sleeve ends by a simple interference fit, or they may be attached via an adhesive, heat treatment or other well-known assembly process for plastic materials.

Figure 4A:
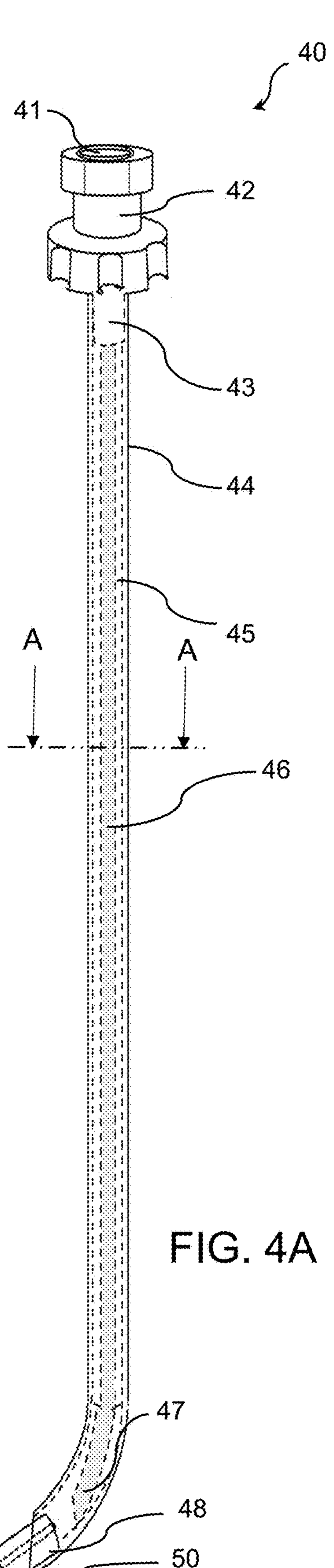
FIG. 4A is a diagrammatic perspective view showing a combination ETT stylet according to an embodiment of the invention.
Figure 4B:
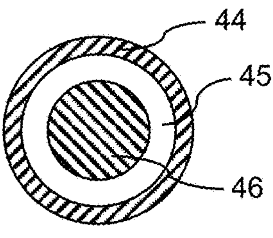
FIG. 4B is a cross-sectional view taken along line A-A of FIG. 4A.
Figure 5:
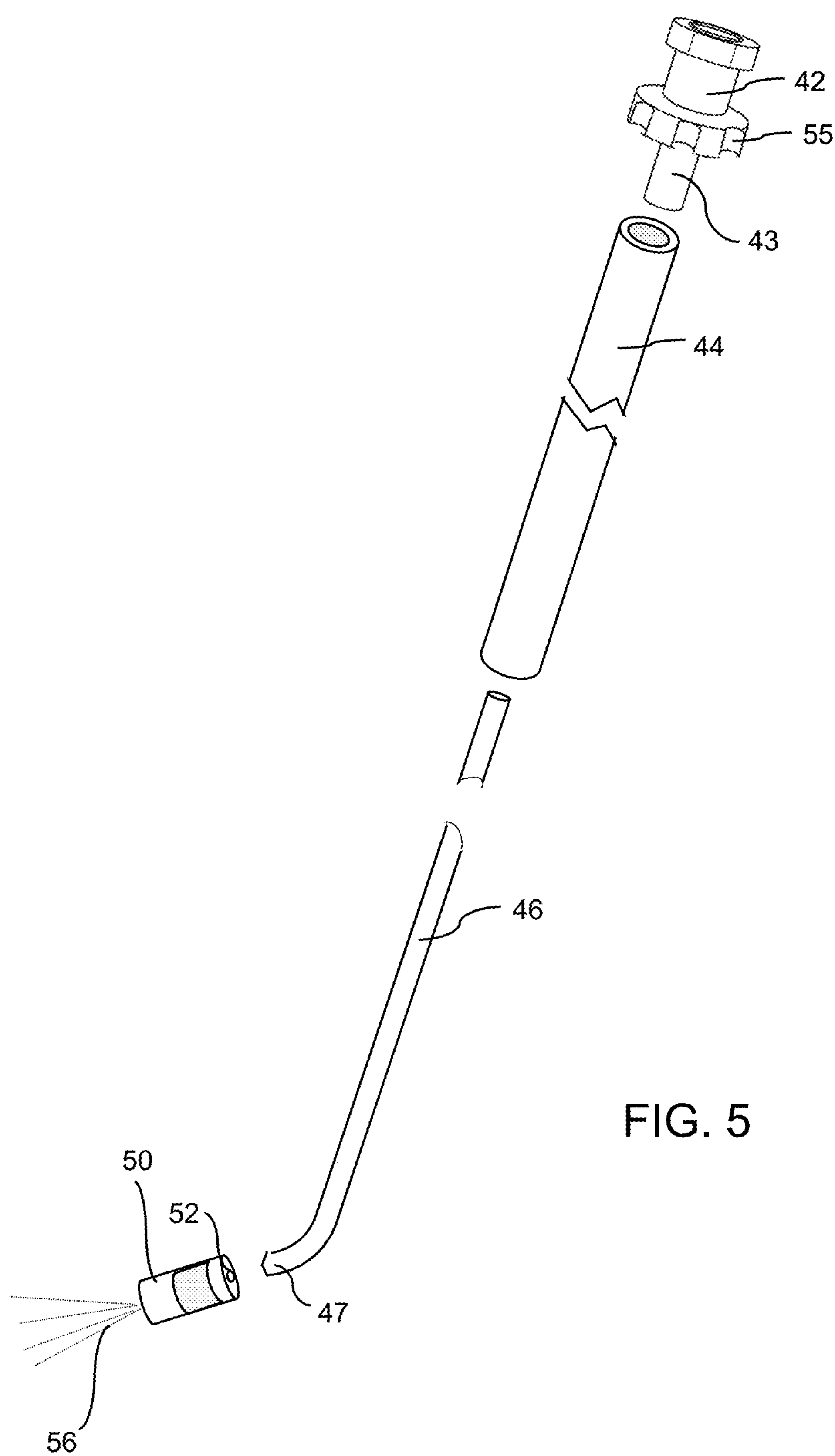
FIG. 5 is an exploded perspective view of the embodiment of FIG. 4A
Figures 6A, 6B:
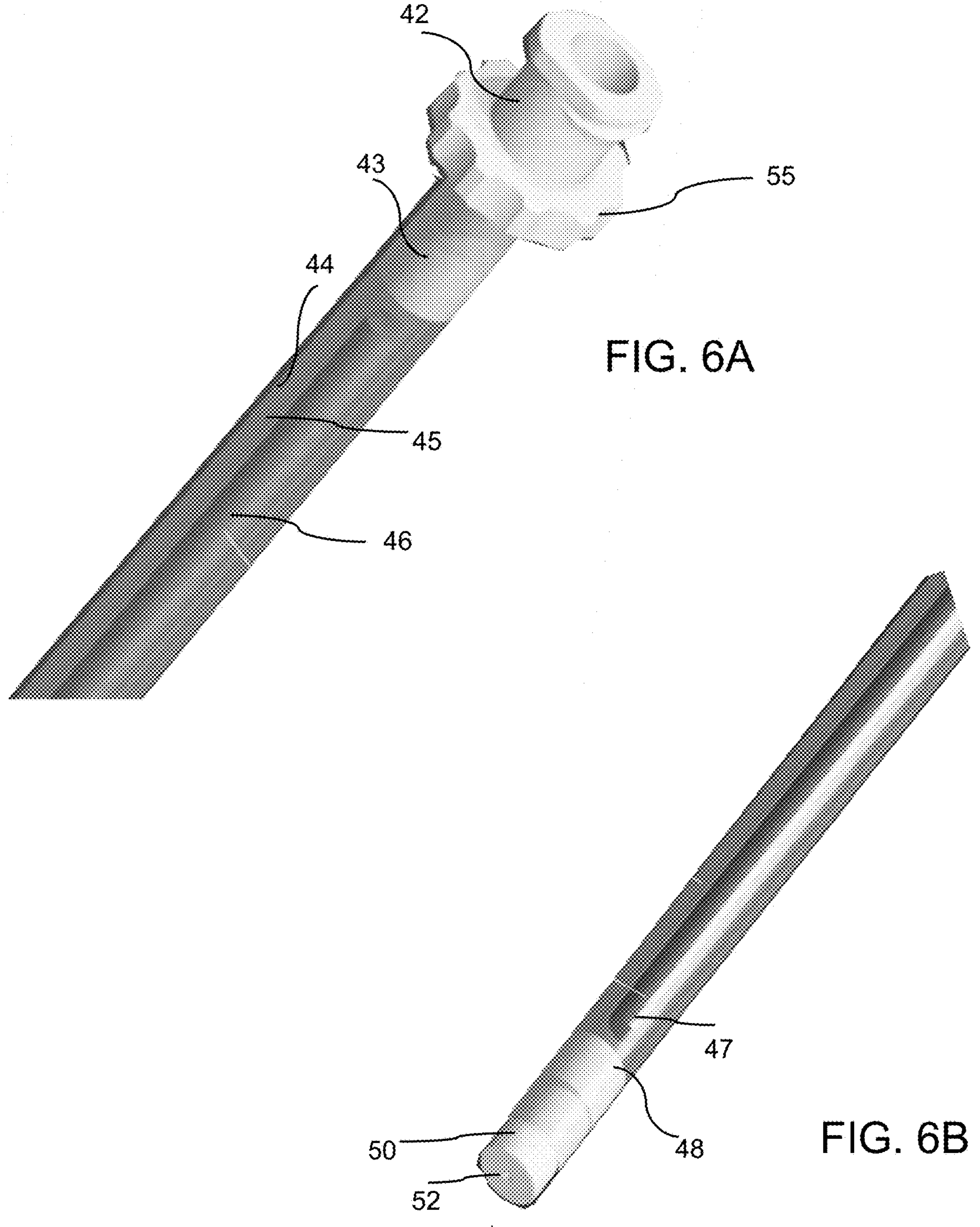
FIGS. 6A and 6B are detail views of the proximal and distal ends, respectively, of the combination ETT stylet according to an embodiment of the invention.

As shown in FIGS. 4A, 6A and 6B, the length of guiding stylet 46 is slightly less than the length of sleeve 44. These small gaps ensure that the injected liquid is able to enter channel 45 at the proximal end of sleeve 44 without obstruction by the proximal end of guiding stylet 46, as well as entering bore 52 without obstruction by distal end 47 of the stylet.

Figure 7:
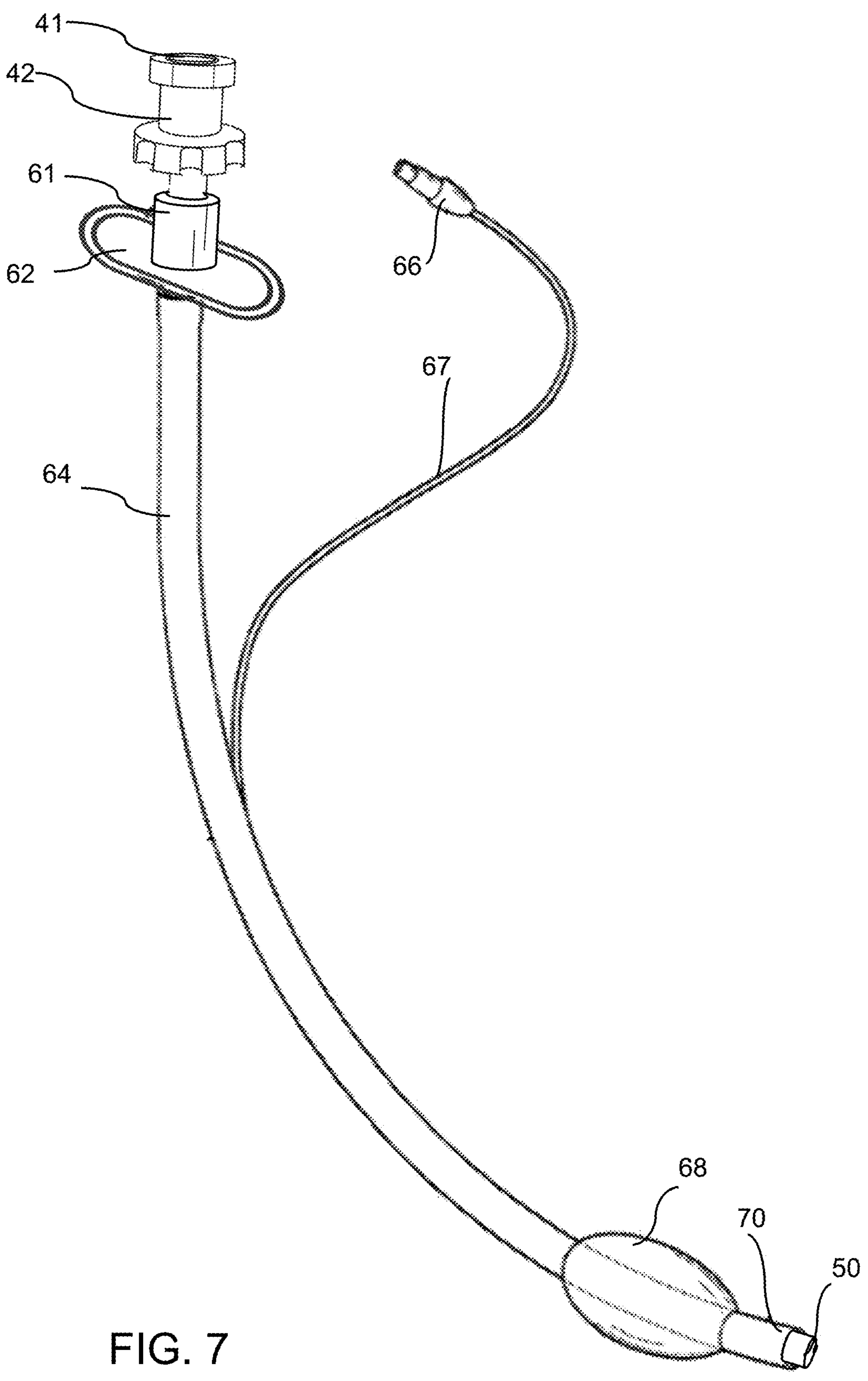
FIG. 7 is a perspective view of a ETT with the ETT stylet.
Figure 8:
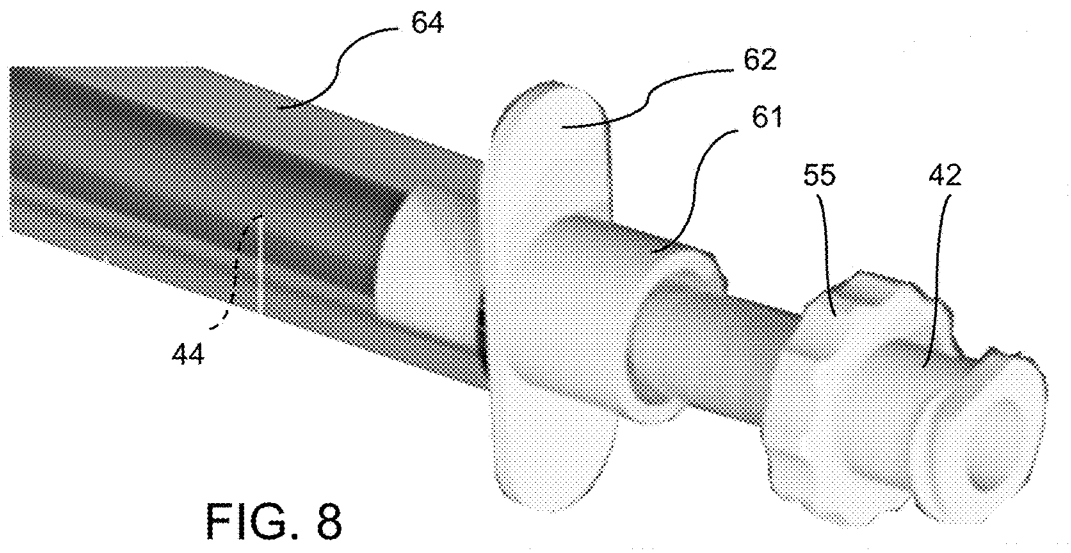
FIG. 8 is a detail view of the proximal end of the ETT and ETT stylet.

Referring to FIG. 7, the inventive ETT stylet 40 is shown inserted into the proximal end 61 of an ETT (such as that shown in FIG. 1) with fitting 42 extending out of the ETT, leaving opening 41 accessible for injection of a medication via a syringe or other injector. Flange 55 on fitting 42 acts as an insertion stop to prevent the ETT stylet from over-insertion of the device past the desired distal tip of the endotracheal tube. ETT shoulder 62 provides a handle for manipulation of the ETT as well as a surface to apply a counter pressure to facilitate the motion needed to insert and slide the inventive ETT stylet into the ETT tube 64 as well as to hold the ETT in place when using a syringe to inject a medication into ETT stylet. The length of ETT stylet 40 is approximately the same as the overall length of the ETT, as indicated by the protrusion of nozzle 50 from the distal end 70 of ETT tube 64. This allows the administration of a fine mist or spray of medication which can be directed at target tissues in the patient's anatomy (such as the vocal cords, larynx, trachea, or other desired structures) to anesthetize the tissue during intubation as well as to administer additional medications as needed after the patient has been intubated. As with prior art ETTs, a fitting 66 on the proximal end of fine tubing 67 provides for the introduction/release of pressurized air to expand/deflate inflatable cuff 68. FIG. 8 provides a detailed view of the proximal end of ETT stylet 40 as inserted into ETT 60 with the elements as described with reference to FIG. 7.

Figure 9:
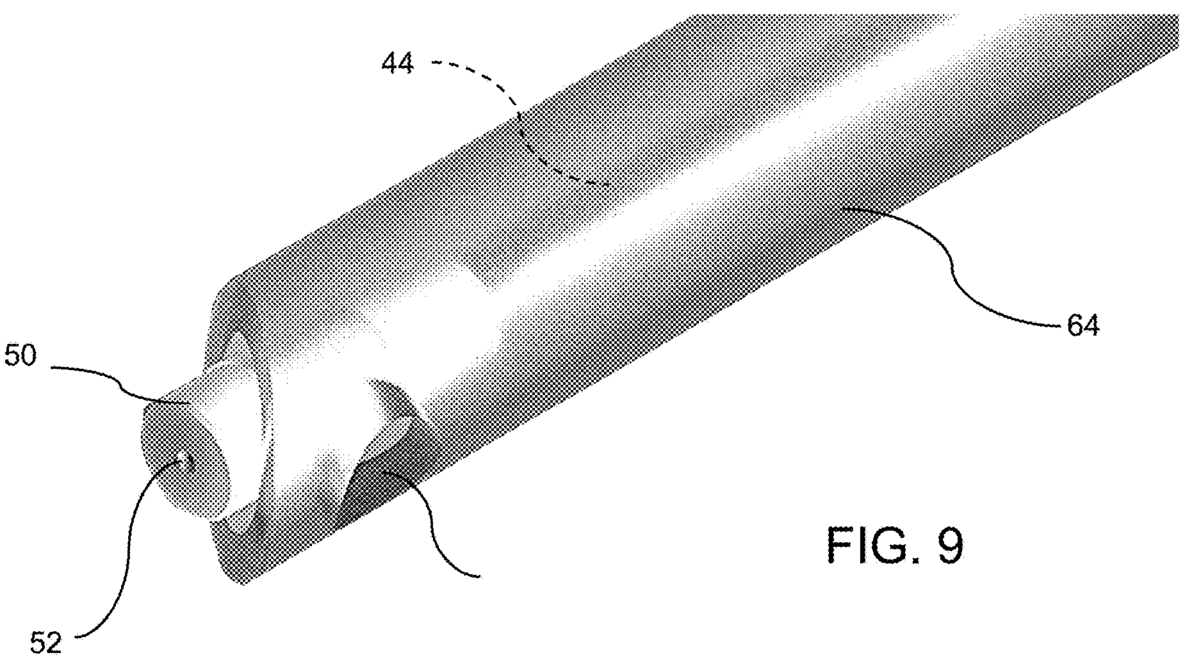
FIG. 9 illustrates an alternative configuration of the inventive ETT stylet inserted within an ETT.

FIG. 9 illustrates an alternative configuration of the inventive ETT stylet inserted within an ETT. In this embodiment, the distal end 4 of the inventive stylet 40, represented by nozzle 50, terminates at the same level as the distal end of the endotracheal tube 64. A Murphy eye 66 is formed near the distal end of a standard endotracheal tube. This configuration allows medication to be administered outside of the tip of the endotracheal tube, but without the ETT stylet extending past the end of the endotracheal tube, thus reducing the risk of tracheal injury from the stylet.

Figure 10:
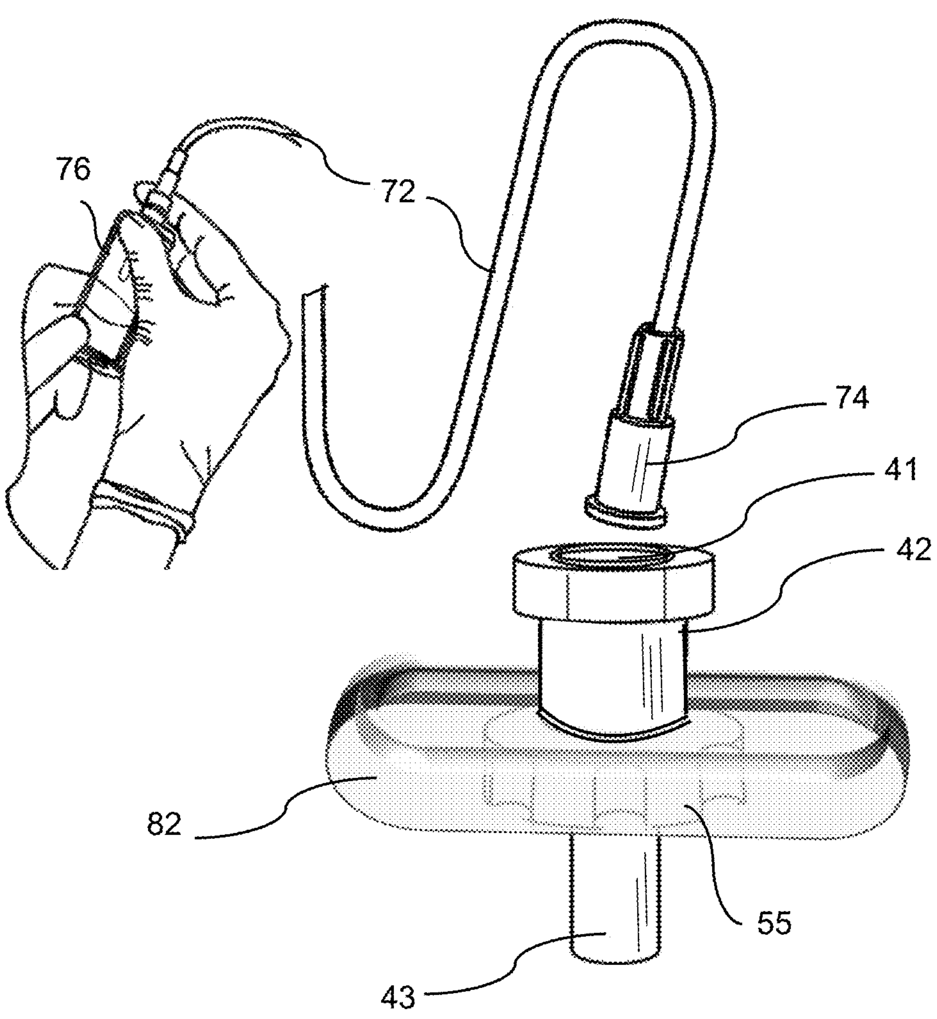
FIG. 10 is a diagrammatic view of an embodiment of the proximal end of the inventive stylet with optional features for medication administration and an insertion stop.

FIG. 10 illustrates additional features that can be utilized with the inventive ETT stylet. As previously noted, it is sometimes necessary to administer medication to a patient who is in the process of being intubated, or after the ETT has been inserted. For example, in a "code blue" situation where the patient is in arrest but no intravenous access is present, the inventive ETT stylet can be used to administer medication such as epinephrine, atropine, etc. In conventional ETTs, such procedures can be ineffective due to absorption of the medication into the plastic endotracheal tube. Sleeve 44 of the inventive device is constructed of materials that are not subject to such limitations. Medication can be easily administered by inserting a mating fitting 74 into opening 41 of fitting 42 of the ETT stylet. The proximal end of fine tubing 72 includes a standard fitting configured to permit attachment or insertion of a syringe 76 for injection of the appropriate medication. The length of tubing 72 can be such that an assistant can administer the medication from the side within interfering with the practitioner, who is focused on the intubation procedure or other medical needs of the patient.

A second feature shown in FIG. 10 is a shoulder stop 82 that can be removably attached to the ETT stylet to limit the insertion of the ETT stylet to prevent the device from extending past the distal tip of the endotracheal tube. Shoulder stop 82 may be formed from rubber, silicon, PDMS, or a similar resilient material. As illustrated, shoulder stop 82 sits atop flange 55, but it may be positioned at different locations along the length of ETT stylet to vary the insertable length of the device. This variability would allow the combination ETT stylet to be used for any number of different sized endotracheal tubes. It should be noted that the two additional features are illustrated in the same figure for expediency only, and they can be used as separate add-ons to the inventive device.

Figure 11:
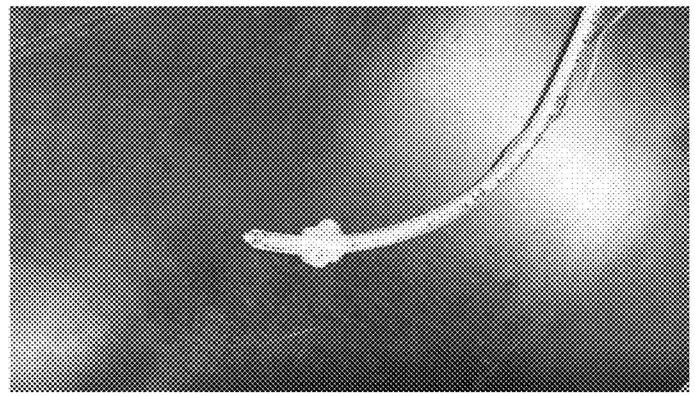
FIG. 11 is a series of photographs of a prototype of the inventive design as used to produce a spray.
Figure 11:
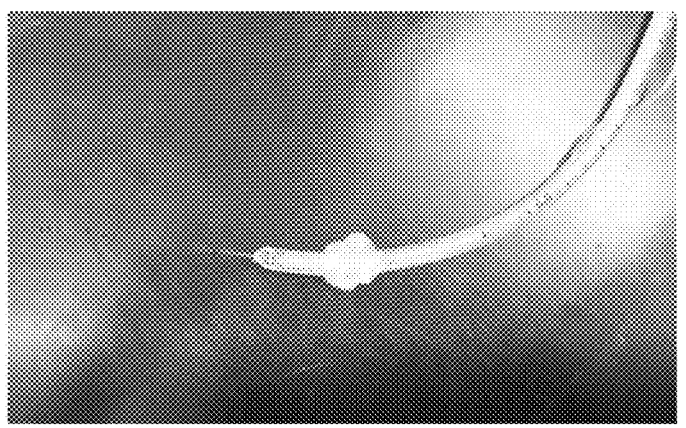
Figure 11:
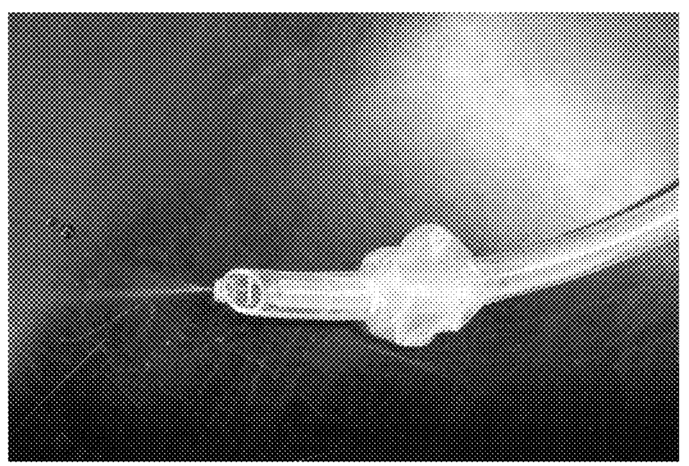
Figure 11:
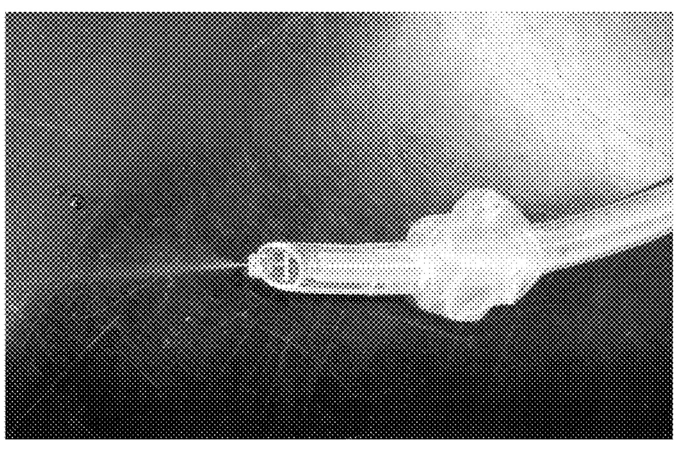

FIG. 11 is a set of photographs showing a prototype of the inventive ETT stylet inserted into a typical endotracheal tube. The top image shows the ETT prior to application of pressure. The second image shows initiation of the fluid spray. The third and fourth images show a well-dispersed fine spray being generated at the distal end of the device.

The present invention contemplates any number of combinations and variations in which the features of a form-guiding stylet along with that of a medicinal delivery cannula are combined into single assembly for insertion into and providing guidance for an endotracheal tube during intubation along with both pre-procedure and post-procedure anesthetizing of the patient's trachea. For example, the inner stylet material and configuration may include any type of solid, mesh, grid, coil, or weave construction the forms an elongated structure of malleable and bendable (soft) metal, which can be integrated into the sleeve-shaped wall of a silastic (i.e., defined as sanitary and flexible plastic) body of the device. Other variations and combinations of elements disclosed herein will become readily apparent to those in the art based on the teaching of the present disclosure.

The invention claimed is:

1. A combination stylet device for use in guiding an endotracheal tube during an intubation procedure, the device comprising:

an elongated sleeve having a hollow interior, a sleeve inner diameter, and a sleeve length;

a fitting disposed at a proximal end of the sleeve, the fitting having a connector opening configured for mating with a syringe and a cylindrical extension having an outer diameter configured to closely fit the sleeve inner diameter at the proximal end of the sleeve;

a nozzle disposed at a distal end of the sleeve, the nozzle comprising a cylindrical body having an outer diameter configured to closely fit the sleeve inner diameter at the distal end of the sleeve to form a liquid-tight seal, the cylindrical body having a concentric bore extending therethrough with an outlet at a distal tip, wherein the outlet is configured to project a fine spray axially forward beyond the distal tip when a pressurized liquid is introduced into the sleeve; and an elongated bendable guiding stylet disposed coaxially within the sleeve between the fitting and the nozzle, the stylet having a stylet diameter and a stylet length, wherein the stylet diameter is smaller than the first inner diameter so that a channel is defined between an outer surface of the guiding stylet and an inner surface of the sleeve, and wherein the stylet length is less than the sleeve length so that a gap is defined between a distal end of the stylet and a proximal end of the nozzle, wherein pressurized liquid introduced through the fitting into the sleeve is communicated by the channel and the gap to the bore of the nozzle;

wherein the sleeve is configured for insertion into the endotracheal tube during intubation, and wherein the sleeve length is configured to position the nozzle near to and partially protruding from a distal end of the endotracheal tube while the combination stylet device only projects the fine spray axially forward the distal end of the endotracheal tube.

2. The device of claim 1, wherein the fitting is configured for releasable attachment to the syringe, and wherein the syringe generates sufficient pressure to force liquid in the syringe out of the nozzle.

3. The device of claim 1, wherein the liquid is a topical anesthetic.

4. The device of claim 1, wherein the fitting further comprises an insertion stop configured to limit an insertion length within the endotracheal tube.

5. The device of claim 1, wherein the fitting comprises a Luer-style fitting configured for releasably mating with a Luer-style syringe.

6. The device of claim 1, further comprising a connector disposed at an end of an elongated tubing, the connector configured for releasably mating with the fitting and the elongated tubing having a length configured to allow administration of additional liquids at a non-interfering distance from the intubation procedure.

7. The device of claim 1, further comprising a removable stop configured for attachment to the fitting or the sleeve to limit insertion of the device to a predetermined insertion depth within the endotracheal tube.

8. A stylet device for guiding an endotracheal tube during intubation, the device comprising:

an elongated cylindrical sleeve having a hollow interior and a sleeve length, the sleeve formed from a flexible medical grade plastic material;

an elongated bendable guiding stylet disposed coaxially within the sleeve, the guiding stylet having a stylet length and an outer diameter smaller than an inner diameter of the sleeve so that a channel is defined between the guiding stylet and the sleeve;

a fitting disposed at a proximal end of the sleeve to define a liquid-tight seal, the fitting having a connector opening configured for mating with a syringe; and a nozzle disposed at a distal end of the sleeve, the nozzle comprising a cylindrical body having an outer diameter configured to closely fit the sleeve inner diameter at the distal end of the sleeve to form a liquid-tight seal, the cylindrical body having a concentric bore with an outlet at a distal tip, wherein the stylet length is less than the sleeve length so that a gap is defined between a distal end of the guiding stylet and a proximal end of the nozzle, wherein pressurized liquid introduced through the fitting into the sleeve is communicated by the channel and the gap to the bore of the nozzle, wherein the outlet is configured to project a fine spray of the liquid axially forward beyond the distal tip;

wherein the sleeve is configured for coaxial insertion into the endotracheal tube during intubation, and wherein the sleeve length is configured to position the nozzle near to and partially protruding from a distal end of the endotracheal tube while the combination stylet device only projects the fine spray axially forward the distal end of the endotracheal tube.

9. The device of claim 8, wherein the fitting is configured for releasable attachment to the syringe, and wherein the syringe is configured to generate the pressure.

10. The device of claim 8, wherein the liquid is a topical anesthetic.

11. The device of claim 8, wherein the fitting further comprises an insertion stop configured to limit an insertion length within the endotracheal tube.

12. The device of claim 8, wherein the fitting comprises a Luer-style fitting configured for releasably mating with a Luer-style syringe.

13. The device of claim 8, further comprising a connector disposed at an end of an elongated tubing, the connector configured for releasably mating with the fitting and the elongated tubing having a length configured for administration of additional liquids at a non-interfering distance from the intubation procedure.

14. The device of claim 8, further comprising a removable stop configured for attachment to the fitting or the sleeve to limit insertion of the device to a predetermined insertion depth within the endotracheal tube.

* * * * *